United States Patent
Dennis-Smither et al.

(10) Patent No.: US 12,084,409 B2
(45) Date of Patent: *Sep. 10, 2024

(54) PROCESS FOR DEHYDRATING METHANOL TO DIMETHYL ETHER

(71) Applicants: BP P.L.C., London (GB); BP (CHINA) HOLDINGS LTD, Shanghai (CN)

(72) Inventors: Benjamin James Dennis-Smither, Hull (GB); John Glenn Sunley, Hull (GB); Zhiqiang Yang, Dalian (CN)

(73) Assignees: BP P.L.C., London (GB); BP (CHINA) Holdings LTD, Shanghai (CN)

( * ) Notice: Subject to any disclaimer, the term of this patent is extended or adjusted under 35 U.S.C. 154(b) by 476 days.

This patent is subject to a terminal disclaimer.

(21) Appl. No.: 17/433,118

(22) PCT Filed: Feb. 22, 2019

(86) PCT No.: PCT/CN2019/075818
§ 371 (c)(1),
(2) Date: Aug. 23, 2021

(87) PCT Pub. No.: WO2020/168539
PCT Pub. Date: Aug. 27, 2020

(65) Prior Publication Data
US 2022/0098136 A1  Mar. 31, 2022

(51) Int. Cl.
| | | |
|---|---|---|
| C07C 41/08 | (2006.01) | |
| B01J 29/08 | (2006.01) | |
| B01J 29/18 | (2006.01) | |
| B01J 29/40 | (2006.01) | |
| B01J 29/65 | (2006.01) | |
| B01J 29/70 | (2006.01) | |
| B01J 29/85 | (2006.01) | |
| C07C 41/09 | (2006.01) | |

(52) U.S. Cl.
CPC ............. *C07C 41/09* (2013.01); *B01J 29/084* (2013.01); *B01J 29/18* (2013.01); *B01J 29/40* (2013.01); *B01J 29/65* (2013.01); *B01J 29/70* (2013.01); *B01J 29/7007* (2013.01); *B01J 29/7038* (2013.01); *B01J 29/7042* (2013.01); *B01J 29/7046* (2013.01); *B01J 29/85* (2013.01)

(58) Field of Classification Search
CPC .................................................... C07C 41/09
See application file for complete search history.

(56) References Cited

U.S. PATENT DOCUMENTS

| | | |
|---|---|---|
| 7,202,387 B2 | 4/2007 | Shoji et al. |
| 9,212,117 B2 | 12/2015 | Daniel et al. |
| 9,302,253 B2 | 4/2016 | Clark et al. |
| 9,365,483 B2 | 6/2016 | Clark et al. |
| 9,815,760 B2 | 11/2017 | Bristow |
| 10,071,942 B2 | 9/2018 | Bristow |
| 2006/0135823 A1 | 6/2006 | Jun et al. |
| 2010/0010272 A1 | 1/2010 | Ivanova et al. |

FOREIGN PATENT DOCUMENTS

| | | |
|---|---|---|
| EP | 0845294 A2 | 6/1998 |
| EP | 3131867 A1 | 2/2017 |
| WO | 2007006238 A1 | 1/2007 |
| WO | 2014/174107 A1 | 10/2014 |
| WO | 2015/193185 A1 | 12/2015 |

OTHER PUBLICATIONS

International Search Report and Written Opinion of the International Searching Authority for International Application No. PCT/CN2019/075818, completed Nov. 17, 2019.

*Primary Examiner* — Medhanit W Bahta
(74) *Attorney, Agent, or Firm* — McDonnell Boehnen Hulbert & Berghoff LLP

(57) ABSTRACT

A process for dehydrating methanol to dimethyl ether product in the presence of a catalyst and a promoter, wherein the catalyst is at least one aluminosilicate zeolite, and the promoter is selected from one or more compounds of Formula I: (I) wherein each of X and any or all of the Y's may independently be selected from hydrogen, halide, a substituted or unsubstituted hydrocarbyl substituent, or a compound of the formula —CHO, —CO₂R, —COR, or —OR, where R is hydrogen or a substituted or unsubstituted hydrocarbyl substituent, and wherein the molar ratio of promoter to methanol is maintained at less than 1.

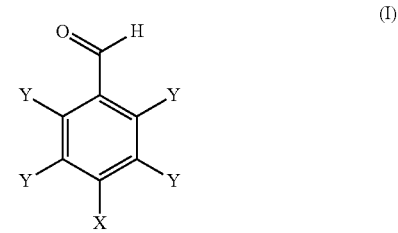

21 Claims, No Drawings

PROCESS FOR DEHYDRATING METHANOL TO DIMETHYL ETHER

This application is a national stage application under 35 U.S.C. § 371 of International Application No. PCT/CN2019/075818, filed Feb. 22, 2019, the disclosure of which is explicitly incorporated by reference herein.

This invention relates in general to a dehydration process and in particular to a process for the dehydration of methanol in the presence of a zeolite catalyst and a promoter compound.

Industrial processes for the dehydration of methanol to dimethyl ether using non-zeolitic catalysts such as alumina are known. Such processes employing alumina catalysts are described, for example in EP-A-1396483.

Processes for the dehydration of alcohols such as methanol employing zeolite catalysts are known and described, for example in WO 2004/074228.

WO 2004/074228 describes a process for preparing dimethyl ether in high yield by employing a dual-catalyst system. Methanol is initially dehydrated over a hydrophilic solid acid catalyst such as gamma-alumina: unreacted methanol is then dehydrated over a second solid acid catalyst, a hydrophobic zeolite such as ZSM-5.

EP-A-1396483 and WO 2004/074228 exemplify the use of high reaction temperatures, typically 250° C. and higher. Whilst the use of such high reaction temperatures may be desirable to achieve acceptable reaction rates, a disadvantage is that at temperatures, typically in excess of 250° C., hydrocarbons are co-produced with the dimethyl ether product and this typically leads to a reduction in catalytic performance.

WO 2011/027105 describes a process for the simultaneous dehydration of methanol and hydrolysis of methyl acetate. The process can be conducted at reaction temperatures below 250° C. by employing a zeolite having a 2-dimensional framework structure comprising at least one channel having a 10-membered ring. Examples of such zeolites are zeolites of framework type FER typified by ferrierite and HEU typified by clinoptilolite.

Processes for the co-production of acetic acid and dimethyl ether by the dehydration of methanol and hydrolysis of methyl acetate in the presence of zeolites having a 2-dimensional framework structure are also described, for example in WO 2013/124404 and WO 2013/124423.

Processes in which methanol-containing streams are dehydrated over solid acid catalysts such as heteropolyacids, gamma-aluminas or zeolites are described, for example in WO 2015/193186 and WO 2015/193188.

Applicant has now found that benzaldehyde and substituted benzaldehyde compounds have a beneficial effect on the rate of dehydration of methanol reactions carried out in the presence of aluminosilicate zeolites Accordingly, the present invention provides a process for dehydrating methanol to dimethyl ether product in the presence of a catalyst and a promoter, wherein the catalyst is at least one aluminosilicate zeolite, and the promoter is selected from one or more compounds of Formula I:

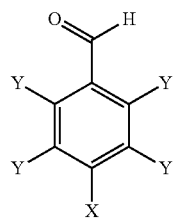

(Formula I)

wherein each of X and any or all of the Y's may independently be selected from hydrogen, halide, a substituted or unsubstituted hydrocarbyl substituent, or a compound of the formula —CHO, —CO$_2$R, —COR, or —OR, where R is hydrogen or a substituted or unsubstituted hydrocarbyl substituent, and wherein the molar ratio of promoter to methanol is maintained at less than 1. Advantageously, the promoters of the present invention allow productivity to dimethyl ether product to be improved in dehydration reactions of methanol which are carried out in the presence of aluminosilicate zeolites, preferably comprising at least one channel having a 10-membered ring.

Also, according to the present invention there is provided a method of improving the productivity to dimethyl ether product in a process for dehydrating methanol in the presence of a catalyst and a promoter, wherein the catalyst is at least one aluminosilicate zeolite, and the promoter is selected from one or more compounds of Formula I:

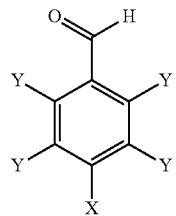

(Formula I)

wherein each of X and any or all of the Y's may independently be selected from hydrogen, halide, a substituted or unsubstituted hydrocarbyl substituent, or a compound of the formula —CHO, —CO$_2$R, —COR, or —OR, where R is hydrogen a substituted or unsubstituted hydrocarbyl substituent, and wherein the molar ratio of promoter to methanol is maintained at less than 1.

Yet further according to the present invention there is provided the use of a promoter in a process for the catalytic dehydration of methanol to dimethyl ether to improve productivity to dimethyl ether product, wherein the catalyst is at least one aluminosilicate zeolite, and the promoter is selected from one or more compounds of Formula I:

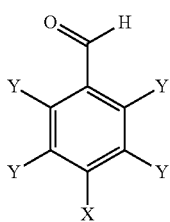

(Formula I)

wherein each of X and any or all of the Y's may independently be selected from hydrogen, halide, a substituted or unsubstituted hydrocarbyl substituent, or a compound of the formula —CHO, —CO₂R, —COR, or —OR, where R is hydrogen or a substituted or unsubstituted hydrocarbyl substituent, and wherein the molar ratio of promoter to methanol is maintained at less than 1.

A further aspect of the present invention provides a process for dehydrating methanol to dimethyl ether product in the presence of a catalyst, wherein the catalyst is at least one aluminosilicate zeolite, and wherein prior to using the catalyst in the dehydration process, the catalyst has been impregnated with a promoter is selected from one or more compounds of Formula I:

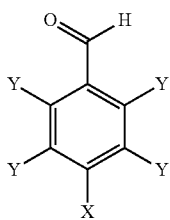

(Formula I)

wherein each of X and any or all of the Y's may independently be selected from hydrogen, halide, a substituted or unsubstituted hydrocarbyl substituent, or a compound of the formula —CHO, —CO₂R, —COR, or —OR, where R is hydrogen or a substituted or unsubstituted hydrocarbyl substituent.

The catalytic dehydration reaction of methanol can be represented by the following equation: 2 methanol⇌dimethyl ether+water.

For use in the present invention, the catalyst belongs to the class of aluminosilicate zeolites. Aluminosilicate zeolites are crystalline microporous materials which have framework structures constructed from tetrahedra of $SiO_4$ and $AlO_4$ that share vertices. Such tetrahedral species are generally referred to as $TO_4$ species wherein the T atom is silicon or aluminium. Aluminium 'T' atoms can be partially or wholly replaced by one or more gallium, boron or iron atoms. For the purposes of the present invention, such gallium, boron or iron modified zeolites are considered to fall within the definition of the term ' aluminosilicate zeolites'.

Silicoaluminophosphate structures containing $PO_4$ tetrahedra are not considered to be aluminosilicate materials and consequently, such silicoaluminophosphates, for example SAPO-type materials, are not within the scope of the present invention.

A zeolite framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC.

A description of zeolites, their framework codes, structure, dimensionality, properties and methods of synthesis can be found in *The Atlas of Zeolite Framework Types* (C. Baerlocher, W. M. Meier, D. H. Olson, 5$^{th}$ Ed. Elsevier, Amsterdam, 2001) in conjunction with its web-based version.

Zeolite crystals contain pore or channel systems of molecular dimensions with fixed geometry and size and can be classified according to the number of channels running in different directions within the zeolite framework structure. A zeolite is described as 1-dimensional, 2-dimensional or 3-dimensional if the zeolite has one, two or three channels in different directions, respectively.

Zeolites may also be classified according to the size of their pores. Zeolite channels with pore openings limited by 8 T atoms in tetrahedral co-ordination are defined as having an 8-membered ring, zeolite channels with pore openings limited by 10 T atoms in tetrahedral co-ordination are defined as having a 10-membered ring, and zeolite channels with pore openings limited by 8 T atoms in tetrahedral co-ordination are defined as having a 12-membered ring. Zeolites can also conveniently be classified based upon the channel containing the largest pore opening, and zeolites with the largest pore openings limited by 8 T atoms in tetrahedral co-ordination (8-membered rings) may be defined as "small pore zeolites" (8-membered rings): zeolites with the largest pore openings limited by 10 T atoms in tetrahedral co-ordination (10-membered rings) may be defined as "medium pore zeolites": and, zeolites with the largest pore openings limited by 12 T atoms in tetrahedral co-ordination (12-membered rings) may be defined as "large pore zeolites".

Non-limiting examples of small pore zeolites are those of framework types CHA, RHO and KFI.

Non-limiting examples of medium pore zeolites are those of framework types TON, MTT, FER, MWW, MFI, EUO, MEL, MFS, and TER.

Non-limiting examples of large pore zeolites are those of framework types, MOR, BEA, FAU, EON, IWV, SEW and USI.

The extent to which the dehydration reaction is promoted may vary depending on factors such as the structure of the zeolite and nature of the promoter employed in the reaction. Desirably, to promote increased productivity to dimethyl ether, the channels of a zeolite must be of a size such that a promoter is able to diffuse freely into the zeolite channels.

In some or all embodiments of the present invention, the catalyst comprises at least one aluminosilicate zeolite which comprises at least one channel having a 10-membered ring. In some or all embodiments of the present invention, the catalyst is an aluminosilicate zeolite which comprises at least one channel having a 10-membered ring.

In some or all embodiments of the present invention, the aluminosilicate zeolite is a medium or large pore zeolite.

In some or all embodiments, the catalyst does not comprise any aluminosilicate zeolite which comprises at least one channel having a 12-membered ring.

In some or all embodiments of the present invention, the aluminosilicate zeolite is a medium pore zeolite.

In some or all embodiments of the present invention, the aluminosilicate zeolite is a medium pore zeolite having a 2-dimensional or a 3-dimensional framework structure. Non-limiting examples of medium pore zeolite having a 2-dimensional or a 3-dimensional framework structure are those of framework types, FER, MWW, MFI and MEL.

In some or all embodiments of the present invention, the aluminosilicate zeolite has the framework type FER, MWW, MFI or MEL, for example the zeolites ferrierite, PSH-3, ZSM-5, ZSM-11, ZSM-35, and MCM-22.

Typically, zeolites are synthesised from synthesis mixtures comprising a silica source, an alumina source, alkali metal hydroxide and water in desired proportions. The synthesis mixture is maintained, with or without agitation, under temperature, pressure and time conditions sufficient to form a crystalline aluminosilicate zeolite. The resulting zeolite contains alkali metal as a cation. Such cations may be replaced by known ion-exchange techniques. For example, the zeolite may be contacted with aqueous solutions of ammonium salts to substitute ammonium ions for the alkali metal cations. Ammonium-form zeolites are also available commercially.

Whilst zeolites in their ammonium-form can be catalytically active, for use in the present invention it is preferred to utilise a zeolite in its hydrogen-form (H-form). H-form zeolites are commercially available. Alternatively, an ammonium-form zeolite can be converted to the H-form by known techniques, for example by calcining the ammonium-form zeolite, in air or inert gas, at high temperature.

In some or all embodiments of the present invention, the zeolite is a hydrogen-form (H-form) zeolite.

For use in the present invention, a zeolite may be composited with at least one binder material. The binder material may be a refractory inorganic oxide, such as silicas, aluminas, alumina-silicates, magnesium silicates, magnesium aluminium silicates, titanias and zirconias.

For use in the present invention the relative proportions of zeolite and binder material in the composite may vary widely. Suitably, the binder material can be present in an amount of from 10% to 90% by weight of the composite.

For use in the present invention, the silica to alumina molar ratio of a zeolite may vary widely but suitably is in the range 10 to 300, for example in the range 20 to 280, such as in the range 20 to 100.

Promoter compounds for use in the present invention are selected from one or more compounds of Formula I:

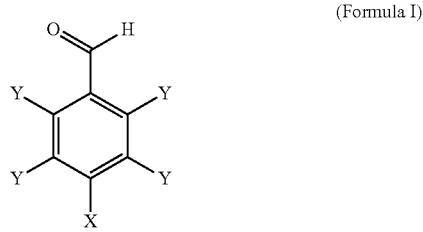

(Formula I)

wherein each of X and any or all of the Y's may independently be selected from hydrogen, halide, a substituted or unsubstituted hydrocarbyl substituent, or a compound of the formula —CHO, —CO$_2$R, —COR, or —OR, where R is hydrogen or a substituted or unsubstituted hydrocarbyl substituent.

In some or all embodiments of the present invention, all of the Y's are hydrogen and X is selected from hydrogen, halide, a substituted or unsubstituted hydrocarbyl substituent, or a compound of the formula —CHO, —CO$_2$R, —COR, or —OR, where R is hydrogen or a substituted or unsubstituted hydrocarbyl substituent.

In some or all embodiments of the present invention, each of X and any or all of the Y's may independently be selected from hydrogen, halide, or a substituted or unsubstituted hydrocarbyl substituent.

In some or all embodiments of the present invention, all of the Y's is hydrogen and X may be selected from hydrogen, halide, or a substituted or unsubstituted hydrocarbyl substituent.

In some or all embodiments of the present invention, the substituted or unsubstituted hydrocarbyl substituent is a substituted or unsubstituted hydrocarbyl substituent comprising from 1 to 11 carbon atoms, preferably 1 to 9 carbon atoms, more preferably 1 to 7 carbon atoms, for example 1 to 6 carbon atoms.

By the term substituted hydrocarbyl as used herein, it is meant a hydrocarbyl component which comprises one or more heteroatoms. The one or more heteroatoms may conveniently be independently selected from nitrogen, oxygen, or a halide.

In the embodiments were X and/or any of the Y's are selected from a compound of the formula —CHO, —CO$_2$R, —COR, or —OR, where R is hydrogen or a substituted or unsubstituted hydrocarbyl substituent, R is preferably selected from a methyl, ethyl, n-propyl, or n-butyl group, more preferably selected from methyl and ethyl, for example a methyl group.

In some or all embodiments, where X and/or any of the Y's are a substituted hydrocarbyl substituent, it is a halide substituted hydrocarbyl. In some or all embodiments, where X is a substituted hydrocarbyl substituent, it is a halide substituted hydrocarbyl.

In the embodiments where X and/or any of the Y's are selected from a substituted or unsubstituted hydrocarbyl substituent, the substituted or unsubstituted hydrocarbyl substituent may be linear or branched, and may be saturated or unsaturated. In the embodiments where X is selected from a substituted or unsubstituted hydrocarbyl substituent, the substituted or unsubstituted hydrocarbyl substituent may be linear or branched, and may be saturated or unsaturated.

In some or all embodiments, X and/or any of the Y's are selected from a substituted or unsubstituted hydrocarbyl substituent. In some or all embodiments, X is selected from a substituted or unsubstituted hydrocarbyl substituent and all of the Y's are hydrogen.

In some or all embodiments, X and/or any of the Y's are selected from an unsubstituted hydrocarbyl substituent comprising from 1 to 11 carbon atoms, preferably 1 to 9 carbon atoms, more preferably 1 to 7 carbon atoms, for example 1 to 6 carbon atoms. In some or all embodiments, X is selected from an unsubstituted hydrocarbyl substituent comprising from 1 to 11 carbon atoms, preferably 1 to 9 carbon atoms, more preferably 1 to 7 carbon atoms, for example 1 to 6 carbon atoms, and all of the Y's are hydrogen.

In some or all embodiments, X and/or any of the Y's are selected from a substituted hydrocarbyl substituent comprising from 1 to 11 carbon atoms, preferably 1 to 9 carbon atoms, more preferably 1 to 7 carbon atoms, for example 1 to 6 carbon atoms: in some or all embodiments, X and/or any of the Y's are a halide substituted hydrocarbyl. In some or all embodiments, X is selected from a substituted hydrocarbyl substituent comprising from 1 to 11 carbon atoms, preferably 1 to 9 carbon atoms, more preferably 1 to 7 carbon atoms, for example 1 to 6 carbon atoms, and all of the Y's are hydrogen; in some or all embodiments, X is a halide substituted hydrocarbyl and all of the Y's are hydrogen.

In the embodiments of the present invention where the catalyst is an aluminosilicate zeolite which comprises at least one channel having an 8-membered ring, or an aluminosilicate zeolite which comprises at least one channel having a 10-membered ring which is 1-dimensional or 2-dimensional, all of the Y's are preferably selected from hydrogen or a halide, more preferably hydrogen.

In the embodiments of the present invention wherein all of the Y's are hydrogen, Formula I may be conveniently written as Formula II below:

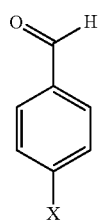

(Formula II)

wherein X is as defined above in relation to Formula I.

In the present invention, a promoter may be added as a component of the feed to the dehydration process. Alternatively and/or additionally, a promoter may be generated in-situ by the addition to the process of any compound or compounds (a precursor compound or precursor compounds) from which compound of Formula I can be generated in-situ.

For example, in-situ generation of the promoter may be accomplished by feeding a di-alkoxy acetal or alkoxy hemiacetal, where the alkoxy groups are methoxy or ethoxy, most preferably methoxy, with the methanol feed.

In the present invention the molar ratio of promoter to methanol is maintained throughout the dehydration reaction at less than 1. In some or all embodiments of the present invention the molar ratio of promoter to methanol is maintained in the range 0.000001:1 to less than 0.5:1, preferably in the range of 0.00005:1 to less than 0.5:1. In some or all embodiments of the present invention, the molar ratio of promoter to methanol is maintained in the range of 0.00001:1 to less than 0.5:1, for example 0.00005:1 to 0.2:1, such as 0.0001:1 to 0.2:1. In some or all embodiments of the present invention, the molar ratio of promoter to methanol is maintained in the range of 0.01:1 to less than 0.5:1, for example 0.01:1 to 0.2:1, such as 0.02:1 to 0.2:1.

Suitably, in the present invention the total amount of promoter relative to the total amount of methanol is maintained throughout the dehydration reaction in an amount of at least 1 ppm. In some or all embodiments of the present invention, the total amount of promoter relative to the total amount of methanol is maintained throughout the dehydration reaction in an amount of at least 0.001 mol %, for example in an amount of 0.001 mol % to less than 50 mol %, such as 0.001 mol % to 20 mol %, for instance 0.005 mol % to 20 mol %. In some or all embodiments of the present invention, the total amount of promoter relative to the total amount of methanol is maintained throughout the dehydration reaction in an amount of at least 0.01 mol %, for example in an amount of 0.01 mol % to less than 50 mol %, such as 0.01 mol % to 20 mol %, for instance 0.05 to 20 mol %. In some or all embodiments of the present invention, the total amount of promoter relative to the total amount of methanol is maintained throughout the dehydration reaction in an amount of at least 1 mol %, for example in an amount of 1 mol % to less than 50 mol %, such as 1 mol % to 20 mol %, for instance 2 to 20 mol %.

In some or all embodiments of the present invention, the catalyst may be impregnated with the promoter prior to being used in the dehydration process. The method of impregnation is not limited and any technique known in the art may be used, for example, incipient wetness technique or excess solution technique. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation. The promoter may be used as the impregnation solution directly, or a dilute solution of the promoter may be used. When a dilute solution of promoter is used, the solvent for the impregnation solution may suitably be an aqueous solution, an organic solution, or a mixture of aqueous and organic solvent(s), depending upon the solubility of the promoter being used; non-limiting examples of suitable solvents include alcohols, for example methanol, ethers, and mixtures thereof, such as aqueous alcoholic solutions, for example an aqueous methanol solution.

Suitably, in the present invention, the dehydration process may be carried out as a standalone process. In such cases the dehydration reaction is not, for example carried out as part of a co-production process, such as co-production processes for the production of acetic acid and dimethyl ether by dehydration of methanol and hydrolysis of a methyl acetate co-feed. Thus, suitably, in the present invention, the feed components to the process are methanol and at least one promoter compound of Formula I or a precursor compound or precursor compounds thereof.

However, typically, the product stream of the methanol dehydration reaction will comprise dimethyl ether, water, unconverted methanol and one or more compounds selected from promoter compounds of Formula I or a precursor compound or precursor compounds thereof. Thus, in some or all embodiments of the present invention, one or more components of the product stream of the dehydration process are recycled as feed to the process. In such instances one or both of dimethyl ether and water are additional feed components to the dehydration process.

Thus, in some or all embodiments of the present invention the feed components to the dehydration process are methanol, at least one promoter selected from Formula I or a precursor compound or precursor compounds thereof, and one or both of dimethyl ether and water.

In instances where it is desired to generate the promoter in situ in the dehydration process the feed components to the process may be methanol and at least one precursor compound of the promoters of Formula I.

Thus, in some or all embodiments of the present invention the feed components to the dehydration process are methanol, one or both of (i) at least one promoter compound of Formula I and (ii) at least one precursor compound of a promoter compound of Formula I; and one or both of dimethyl ether and water.

The feed components to the process may be supplied to the process in one or more feed streams.

The dehydration process is carried out as a heterogeneous process, either as a vapour phase heterogeneous process or as a liquid phase heterogeneous process.

The type of reactor used for the dehydration process is not limited, and it may be suitably carried out in any type of reactor within which a vapour phase heterogeneous process or a liquid phase heterogeneous process may be performed.

Non-limiting types of reactors with which the dehydration reaction may be performed include tank reactors, multi-tubular reactors, plug-flow reactors, loop reactors, fluidized bed reactors, and reactive distillation columns.

The dehydration process may be carried out at a temperature of from 100 to 300° C. In some or all embodiments of the present invention, the dehydration process is carried out at a temperature of from 110 to 250° C., for example from 125 to 200° C.

Suitably, the dehydration process may be carried out at atmospheric pressure or at elevated pressure.

In some or all embodiments of the present invention, the dehydration process is carried out at a total pressure of atmospheric pressure to 3,000 kPa. Where the process is conducted in the liquid phase, higher total pressures, such as 4,000 kPa to 10,000 kPa, may be required to maintain the dimethyl ether product in solution.

In some or all embodiments of the present invention, the dehydration process is carried out as a heterogeneous vapour phase process at a total pressure of atmospheric pressure to 3,000 kPa. In these embodiments, the temperature may be from 100 to 300° C., such as from 140 to 250° C., for example from 150 to 250° C.

For vapour phase processes, the process may be carried out at a total gas hourly space velocity (GHSV) in the range 500 to 80,000 h$^{-1}$, preferably in the range 1,000 to 40,000 h$^{-1}$.

For liquid phase processes, the process may be carried out at a total liquid hourly space velocity (LHSV) in the range 0.2 to 20 h$^{-1}$.

The dehydration process may be carried out using one or more beds of zeolite catalyst, suitably selected from fixed bed, fluidised bed, and moving beds of catalyst.

The dehydration process may be operated as either a continuous or a batch process, preferably as a continuous process.

The dehydration process generates a crude reaction product comprising dimethyl ether and water as reaction products, unreacted methanol and one or more promoter or precursor compounds. One or more components of the crude reaction product may be recycled as feed to the process.

Dimethyl ether may be recovered from the crude reaction product by any suitable method, for example by distillation methods.

Without being bound by theory, the productivity of catalysts will typically decrease over time on stream: in industrially applied catalytic processes, one of the ways by which the decrease in productivity may be compensated for is by increasing the reaction temperature to maintain a consistent productivity. A disadvantage of increasing the temperature of the reaction is that this may lead to an increase in undesirable by-products or may result in a decrease in selectivity: another disadvantage of increasing the temperature of the reaction is that such an increase in temperature may accelerate the rate of catalyst deactivation. However, without wishing to be bound by theory, it is believed that in the present invention, decreases in productivity of the catalyst may be at least in part compensated for by increasing the relative concentration of the promoter in the methanol feed, and thus may reduce or eliminate the need for an increase in temperature to compensate for any reduction in productivity which may occur with time on stream; similarly, decreases in productivity of the catalyst may be at least in part compensated for by changing the promoter used or by adding a second or further additional promoter compound to the methanol feed as the time on stream increases.

In addition to the beneficial effect on the rate of dehydration of methanol reactions carried out in the presence of the catalyst, it is believed that the use of promoters as described herein may result in an increase in the stability of the catalyst and may make the catalyst more resistant to deactivation by impurities present in the methanol feed.

In a further aspect of the present invention provides a process for dehydrating methanol to dimethyl ether product in the presence of a catalyst, wherein the catalyst is at least one aluminosilicate zeolite, and wherein prior to using the catalyst in the dehydration process, the catalyst has been impregnated with a promoter selected from one or more compounds of Formula I:

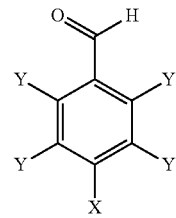

(Formula I)

wherein each of X and any or all of the Y's may independently be selected from hydrogen, halide, a substituted or unsubstituted hydrocarbyl substituent, or a compound of the formula —CHO, —CO$_2$R, —COR, or —OR, where R is hydrogen or a substituted or unsubstituted hydrocarbyl substituent.

In this further aspect of the invention, the feed to the dehydration process comprises methanol and may optionally comprise other components, for example dimethyl ether, water, or at least one compound which is a promoter compound of Formula I or a precursor compound or precursor compounds thereof.

The invention is now illustrated with reference to the following non-limiting Examples.

EXAMPLES

The zeolites and SAPO used in the Examples were utilised in their H-form. The SAPO-34, ferrierite, PSH-3, ZSM-5 mordenite, beta and Y catalysts were obtained from Zeolyst International and the SSZ-13 and ZSM-11 were obtained from ACS Materials. These catalysts were calcined in air at 500° C. for 4 hours prior to use. The ZSM-22 and ZSM-23 was prepared in accordance with literature methods. Details of the zeolites is provided in Table 1 below.

TABLE 1

| Catalyst | SAR* | Framework code | Largest ring size | Structure** |
|---|---|---|---|---|
| SAPO-34 | n/a | CHA | 8 | 3-D |
| SSZ-13 | 18 | CHA | 8 | 3-D |
| ZSM-22 | 61 | TON | 10 | 1-D |
| ZSM-23 | 91 | MTT | 10 | 1-D |
| Ferrierite | 20 | FER | 10 | 2-D |
| PSH-3 | 21 | MWW | 10 | 2-D |
| ZSM-5 (23) | 23 | MFI | 10 | 3-D |
| ZSM-5 (50) | 50 | MFI | 10 | 3-D |
| ZSM-5 (280) | 280 | MFI | 10 | 3-D |
| ZSM-11 | 53 | MEL | 10 | 3-D |
| Mordenite | 20 | MOR | 12 | 1-D |
| Zeolite beta | 25 | BEA | 12 | 3-D |
| Zeolite Y | 30 | FAU | 12 | 3-D |

*SAR indicates the silica to alumina molar ratio of a zeolite.
**1-D, 2-D and 3-D indicate a 1-dimensional, a 2-dimensional and a 3-dimensional zeolite framework structure respectively.

The methanol dehydration reactions of the Examples were carried out utilising the General Reaction Method and Apparatus described below.

General Reaction Method and Apparatus

The methanol dehydration reactions were carried out using a 16-channel parallel fixed-bed stainless steel reactor system. Each reactor (10 mm internal diameter) housed a bed of catalyst mixed with silica dioxide diluent (0.168 g catalyst diluted with 0.337 g silica dioxide). The catalyst and silica dioxide each had a particle size of 450 to 900 microns diameter. The mixture was loaded on top of a 6.5 cm deep bed of an inert material (quartz sand). The reactor volume above the catalyst bed was also packed with quartz sand.

Each reactor was maintained at a temperature of 150° C. and at a total pressure of 1100 kPa throughout the reactions. A gaseous feed comprising 10 mol % methanol and inert gas was introduced into the reactor and allowed to flow through the catalyst bed for at least 24 hours before a promoter compound was added to the feed. Throughout the reactions the methanol feed rate was kept constant at 45 mmol h$^{-1}$. The effluent stream from each reactor was cooled to 5° C. in a condenser and the gas phase from the condenser was periodically analysed by online gas chromatography to determine the yield of dimethyl ether product. Different promoters were added to the feed and the dimethyl ether yield was measured. When introducing the promoter the flow rate of inert gas was adjusted to maintain a constant GHSV of the combined MeOH, promoter and inert gas feed.

Example 1

This Example demonstrates the effect of benzaldehyde co-feed at 0.1 mol % relative to methanol fed, on methanol dehydration reactions employing various catalysts. The methanol dehydration reactions were carried out using the General Reaction Method and Apparatus described above. The observed space time yields to dimethyl ether product are provided in Table 2 below.

TABLE 2

| | Dimethyl ether STY/g kg$^{-1}$ h$^{-1}$ | | |
|---|---|---|---|
| Catalyst | No Promoter | Benzaldehyde (0.1 mol %) | Stability |
| SAPO-34 | 695 | 697 | Good |
| SSZ-13 | 912 | 998 | Good |
| ZSM-22 | 244 | 343 | Good |
| ZSM-23 | 383 | 456 | Good |
| Ferrierite | 1521 | 2550 | Good |
| PSH-3 | 499 | 1955 | Good |
| ZSM-5 (23) | 583 | 1829 | Good |
| ZSM-5 (50) | 407 | 1888 | Good |
| ZSM-5 (280) | 106 | 835 | Good |
| ZSM-11 | 345 | 1811 | Good |
| Mordenite | 722 | 809 | Moderate |

TABLE 2-continued

| | Dimethyl ether STY/g kg$^{-1}$ h$^{-1}$ | | |
|---|---|---|---|
| Catalyst | No Promoter | Benzaldehyde (0.1 mol %) | Stability |
| Zeolite beta | 198 | 666 | Moderate |
| Zeolite Y | 64 | 131 | Moderate |

Some catalysts had moderate stability during introduction of the catalyst co-feed and the percentage decrease in DME STY over a 12-hour period during addition of the co-feed was greater than 5%. The DME STY with no promoter is taken immediately before the promoter was added. The DME STY with the co-feed over the catalysts with good stability is representative of the DME productivity observed during the co-feed period. For the catalysts with moderate stability the DME STY with the co-feed is the maximum DME productivity observed during the co-feed period.

Example 2

This Example demonstrates the effect of benzaldehyde concentration, mole % relative to methanol fed, on methanol dehydration reactions employing 1-, 2- and 3-dimensional zeolite catalysts where the largest ring is 10-membered. The methanol dehydration reactions were carried out using the General Reaction Method and Apparatus described above. The observed space time yields to dimethyl ether product are provided in Table 3 below

TABLE 3

| | Dimethyl ether STY/g kg$^{-1}$ h$^{-1}$ | | | | |
|---|---|---|---|---|---|
| | | Benzaldehyde | | | |
| Catalyst | No Promoter | 0.01 mol % | 0.05 mol % | 0.2 mol % | 0.5 mol % |
| ZSM-22 | 231 | 253 | 294 | 382 | 473 |
| ZSM-23 | 363 | 381 | 407 | 469 | 553 |
| Ferrierite | 1619 | 1719 | 2054 | 2968 | 3875 |
| ZSM-5 (23) | 581 | 867 | 1432 | 2417 | 3387 |
| ZSM-5 (50) | 325 | 739 | 1368 | 2260 | 3057 |
| ZSM-5 (280) | 99 | 325 | 627 | 1051 | 1356 |

The DME STY with no promoter is taken immediately before the promoter was first added. The DME STY with the co-feed is representative of the DME productivity observed during the co-feed period.

Example 3

This Example demonstrates the effect of feeding benzaldehyde and derivatives, 0.1 mole % relative to methanol fed, on methanol dehydration reactions employing a 3-dimensional 10-membered ring zeolite catalyst, ZSM-5. The methanol dehydration reactions were carried out using the General Reaction Method and Apparatus described above. The observed space time yields to dimethyl ether product are provided in Table 4 below.

TABLE 4

| | Dimethyl ether STY/g kg$^{-1}$ h$^{-1}$ | | | | | |
|---|---|---|---|---|---|---|
| Catalyst | No Promoter | Benzaldehyde 0.1 mol % | 4-Trifluoro-benzaldehyde 0.1 mol % | 4-Methyl-benzaldehyde 0.1 mol % | 4-Ethyl-benzaldehyde 0.1 mol % | 4-n-Butyl-benzaldehyde 0.1 mol % |
| ZSM-5 (23) | 563 | 828 | 1712 | 2845 | 2782 | 3307 |
| ZSM-5 (50) | 380 | 836 | 1870 | 3324 | 3405 | 3893 |
| ZSM-5 (280) | 99 | 332 | 778 | 1714 | 1825 | 2120 |

The DME STY with no promoter is taken immediately before the promoter was first added. The DME STY with the co-feed is representative of the DME productivity observed during the co-feed period.

The invention claimed is:

1. A process comprising dehydrating methanol to a dimethyl ether product in the presence of a catalyst and a promoter, wherein the catalyst is at least one aluminosilicate zeolite, and the promoter is selected from one or more compounds of Formula I:

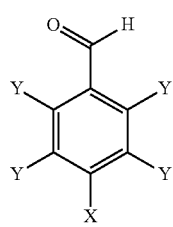

(Formula I)

wherein each of X and any or all of the Y's are independently hydrogen, halide, a substituted or unsubstituted hydrocarbyl substituent, or a group of the formula —CHO, —CO$_2$R, —COR, or —OR, where R is hydrogen or a substituted or unsubstituted hydrocarbyl substituent, and wherein the molar ratio of the promoter to the methanol is maintained at less than 1.

2. A process according to claim 1, wherein the catalyst is at least one aluminosilicate zeolite which comprises at least one channel having a 10-membered ring.

3. A process according to claim 2, wherein the catalyst is an aluminosilicate zeolite which comprises at least one channel having a 10-membered ring.

4. A process according to claim 1, wherein the catalyst does not comprise any aluminosilicate zeolite which comprises at least one channel having a 12-membered ring.

5. A process according to claim 1, wherein the aluminosilicate zeolite is a H-form zeolite.

6. A process according to claim 1, wherein the aluminosilicate zeolite is selected from framework type CHA, TON, MTT, FER, MWW, MFI, MEL, MOR, BEA, and FAU.

7. A process according to claim 6, wherein the aluminosilicate zeolite is selected from framework type FER, MWW, MFI, and MEL.

8. A process according to claim 7, wherein the aluminosilicate zeolite is selected from ferrierite, PSH-3, ZSM-5, ZSM-11, ZSM-35, and MCM-22.

9. A process according to claim 1, wherein the aluminosilicate zeolite is composited with a binder material.

10. A process according to claim 1, wherein X and/or any of the Y's are independently selected from hydrogen, halide, and a substituted or unsubstituted hydrocarbyl substituent comprising from 1 to 11 carbon atoms.

11. A process according to claim 1, wherein X and/or any of the Y's are independently selected from a substituted or unsubstituted hydrocarbyl substituent.

12. A process according to claim 11, wherein X and/or any of the Y's are independently selected from an unsubstituted hydrocarbyl substituent comprising from 1 to 11 carbon atoms.

13. A process according to claim 11, wherein X and/or any of the Y's are independently selected from a substituted hydrocarbyl substituent comprising from 1 to 11 carbon atoms.

14. A process according to claim 13, wherein X and/or any of the Y's are independently a halide substituted hydrocarbyl.

15. A process according to claim 1, wherein all of the Y's are hydrogen.

16. A process according to claim 1, wherein the total amount of the promoter relative to the methanol is maintained in an amount of at least 1 ppm.

17. A process according to claim 1, wherein the molar ratio of the promoter to the methanol is maintained in the range 0.00001:1 to 0.2:1.

18. A process according to claim 1, wherein the process is carried out at a temperature of from 100° C. to 300° C.

19. A process according to claim 1, wherein the process is carried out as a heterogeneous vapour phase process.

20. A process comprising dehydrating methanol to a dimethyl ether product in the presence of a catalyst, wherein the catalyst is at least one aluminosilicate zeolite, and wherein prior to using the catalyst in the dehydration process, the catalyst has been impregnated with a promoter selected from one or more compounds of Formula I:

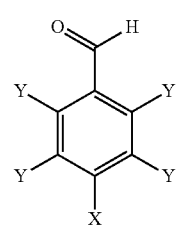

(Formula I)

wherein each of X and any or all of the Y's are independently hydrogen, halide, a substituted or unsubstituted hydrocarbyl substituent, or a group of the formula —CHO, —CO$_2$R, —COR, or —OR, where R is hydrogen or a substituted or unsubstituted hydrocarbyl substituent.

21. A method of improving the productivity to dimethyl ether in a process for dehydrating methanol, the method comprising dehydrating methanol to dimethyl ether in the presence of a catalyst and a promoter, wherein the catalyst is at least one aluminosilicate zeolite, and the promoter is selected from one or more compounds of Formula I:

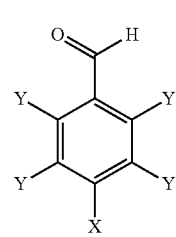

(Formula I)

wherein each of X and any or all of the Y's are independently hydrogen, halide, a substituted or unsubstituted hydrocarbyl substituent, or a group of the formula —CHO, —CO$_2$R, —COR, or —OR, where R is hydrogen or a substituted or unsubstituted hydrocarbyl substituent, and wherein the molar ratio of the promoter to the methanol is maintained at less than 1.

* * * * *